(12) United States Patent
Chen et al.

(10) Patent No.: US 12,185,921 B2
(45) Date of Patent: *Jan. 7, 2025

(54) FLEXIBLE HIGH RESOLUTION ENDOSCOPE

(71) Applicant: SYNAPTIVE MEDICAL INC., Toronto (CA)

(72) Inventors: Sean Jy-Shyang Chen, Toronto (CA); Kamyar Abhari, Toronto (CA); Michael Frank Gunter Wood, Toronto (CA); Gal Sela, Toronto (CA)

(73) Assignee: Synaptive Medical Inc.

( * ) Notice: Subject to any disclaimer, the term of this patent is extended or adjusted under 35 U.S.C. 154(b) by 337 days.

This patent is subject to a terminal disclaimer.

(21) Appl. No.: 17/659,706

(22) Filed: Apr. 19, 2022

(65) Prior Publication Data

US 2022/0233061 A1 Jul. 28, 2022

Related U.S. Application Data

(63) Continuation of application No. 16/326,349, filed as application No. PCT/IB2016/054931 on Aug. 17, 2016, now Pat. No. 11,330,970.

(51) Int. Cl.
*A61B 1/00* (2006.01)
*A61B 1/005* (2006.01)
(Continued)

(52) U.S. Cl.
CPC .............. *A61B 1/045* (2013.01); *A61B 1/005* (2013.01); *A61B 1/0051* (2013.01); *A61B 1/04* (2013.01); *A61B 1/07* (2013.01); *G02B 23/2415* (2013.01); *G02B 23/2469* (2013.01); *A61B 1/01* (2013.01); *A61B 1/0676* (2013.01)

(58) Field of Classification Search
CPC ......... A61B 1/045; A61B 1/0051; A61B 1/07; A61B 1/01; A61B 1/0676; G02B 23/2415; G02B 23/2469
See application file for complete search history.

(56) References Cited

U.S. PATENT DOCUMENTS

| | | | |
|---|---|---|---|
| 4,480,636 A * | 11/1984 | Karaki | G02B 23/2484 348/307 |
| 5,547,455 A | 8/1996 | McKenna et al. | |

(Continued)

FOREIGN PATENT DOCUMENTS

| | | |
|---|---|---|
| WO | 2001045390 | 6/2001 |
| WO | 2018033775 | 2/2018 |

OTHER PUBLICATIONS

Sean Jy-Shyang Chen et al., "A Flexible High Resolution Endoscope", U.S. Appl. No. 16/326,349, filed Feb. 18, 2019, Notice of Allowance issued.

(Continued)

*Primary Examiner* — Timothy J Neal

(57) ABSTRACT

A flexible high-resolution endoscope apparatus and methods involving a plurality of optical fiber bundles; a plurality of lenses in a one-to-one correspondence with the plurality of optical fiber bundles, each lens of the plurality of lenses comprising a distinct depth of field and a distinct angle of view in relation to another lens of the plurality of lenses; and a plurality of cameras in a one-to-one correspondence with the plurality of optical fiber bundles.

18 Claims, 16 Drawing Sheets

(51) Int. Cl.
*A61B 1/04*     (2006.01)
*A61B 1/045*    (2006.01)
*A61B 1/07*     (2006.01)
*G02B 23/24*    (2006.01)
*A61B 1/01*     (2006.01)
*A61B 1/06*     (2006.01)

(56) References Cited

U.S. PATENT DOCUMENTS

| | | | |
|---|---|---|---|
| 11,330,970 B2* | 5/2022 | Chen | A61B 1/005 |
| 2004/0220451 A1* | 11/2004 | Gravenstein | A61B 1/07 600/182 |
| 2005/0219552 A1* | 10/2005 | Ackerman | G01B 11/2536 356/603 |
| 2011/0263938 A1* | 10/2011 | Levy | A61B 1/0684 600/109 |

OTHER PUBLICATIONS

PCT International Search Report for PCT/IB2016/054931 dated Jan. 23, 2017.
PCT Written Opinion of the International Searching Authority for PCT/IB2016/054931 dated Jan. 23, 2017.

\* cited by examiner

FLEXIBLE HIGH RESOLUTION ENDOSCOPE

CROSS-REFERENCE TO RELATED APPLICATION(S)

This document is a continuation application claiming the benefit of, and priority to, U.S. patent application Ser. No. 16/326,349, filed on Feb. 18, 2019, entitled "A Flexible High Resolution Endoscope," and International Application No. PCT/IB2016/054931, filed on Aug. 17, 2016, and entitled "A Flexible High Resolution Endoscope," all of which are hereby incorporated by reference herein in their entirety.

FIELD

The present disclosure generally relates to medical imaging. More particularly, the present disclosure relates to systems and methods for minimally invasive therapy and image guided medical procedures.

BACKGROUND

Traditional flexible endoscopes, also known as fiberscopes, allow for visualization during a minimally invasive procedure. However, these fiberscopes produce two-dimensional images that are devoid of three-dimensional depth information, which is, otherwise, critical to a surgeon attempting to identify, and operate on, small, or difficult to see, structures. Images, acquired by these related art fiberscopes, are also relatively low in quality due to the limited resolution of the fiber bundle used to transmit the images to the sensor. These related art fiberscopes have higher resolution image guides that are still much lower in resolution than current imaging standards. Typical fiber image guides provide images having a resolution of about 18 kilopixels, i.e., much lower when compared to the megapixel resolutions displayed in high-definition video. Furthermore, while some higher resolution image guides are available, this higher resolution is achieved by using thicker optical fiber bundles than those used with typical fiber image guides; and hence higher resolution image guides are constrained in their bending with much larger turning radii that limits where such guides can be used in a surgical case.

SUMMARY

The present disclosure is generally directed to image guided medical procedures using an access port. This port-based surgery approach allows a surgeon, or robotic surgical system, to perform a surgical procedure involving tumor resection in which the residual tumor is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Hence, an aspect of the present disclosure provides a flexible endoscope that produces three-dimensional images, the endoscope comprising multiple fiber bundle image guides (each of which can be around 18 kilopixels resolution), coupled with a multi-lens array on one end and multiple camera sensors on the other end. The fiber bundles in the endoscope are coupled together at a common distal end and, are otherwise, uncoupled from one another. Each lens on the array projects a separate image to a different fiber bundle at the distal end of each fiber bundle, each of which respectively conveys a respective image to a respective camera sensor coupled with an opposite proximal end of each fiber bundle, such that the endoscope acquires a plurality of separate pixelated images. These images, acquired by each of the sensors, are merged and reconstructed by using, for example, principles of light field imaging and processing, to produce a super-resolution image. This merger and reconstruction allow for much higher resolution imaging than is possible with conventional fiberscopes, thereby allowing better diagnosis and treatment. Furthermore, the endoscope provided herein is more flexible than the high-resolution endoscopes as the flexibility is determined by each individual fiber bundle, all of which are coupled together only at a distal end.

An aspect of the present disclosure provides an endoscope comprising: a plurality of optical fiber bundles; a plurality of lenses in a one-to-one relationship with the plurality of optical fiber bundles; and, a plurality of cameras in a one-to-one relationship with the plurality of optical fiber bundles, each respective optical fiber bundle, of the plurality of optical fiber bundles, having a respective lens, of the plurality of lenses, located at a respective distal end, and a camera, of the plurality of cameras, located at a respective proximal end, the plurality of optical fiber bundles being coupled together at a common distal end, and otherwise being uncoupled from one another, a bending radius of the endoscope defined by a largest respective bending radius of each of the plurality of optical fiber bundles.

The plurality of optical fiber bundles comprises a first optical fiber bundle and a second optical fiber bundle, each having the respective lens located at the respective distal end, and the respective camera located at the respective proximal end, thereby forming a three-dimensional camera. Respective distal ends of the plurality of optical fiber bundles, and respective lenses located at the respective distal ends, can be spaced apart from one another to provide different views of objects in front of the respective distal ends, thereby forming a plenoptic camera. Each respective diameter of the plurality of optical fiber bundles can be less than or equal to about 2 mm. The plurality of lenses is each formed in a common optical element that can be located at the common distal end. The plurality of lenses can each be formed in a common optical element located at the common distal end, the common optical element being one or more of: removable from the common distal end of the plurality of optical fiber bundles; and disposable. Two or more of the plurality of lenses can have one or more of: different depths of field, different fields of view of objects in front of the plurality of lenses: and different angular views of objects in front of the plurality of lenses.

The endoscope further comprises a controller configured to: receive respective images from each of the plurality of cameras; and combine the respective images into a single higher resolution image. The endoscope further comprises a controller configured to: receive respective images from each of the plurality of cameras; remove dead pixels from the respective images; and combine the respective images into a single higher resolution image. The endoscope further comprises a controller configured to: receive respective images from each of the plurality of cameras; and combine the respective images into a depth-map of objects in front of the plurality of lenses. The endoscope further comprises a controller configured to: receive respective images from each of the plurality of cameras; and combine the respective images into a depth-map of objects in front of the plurality of lenses using light field processing.

Another aspect of the present disclosure provides a method comprising: at an endoscope having: a plurality of optical fiber bundles; a plurality of lenses in a one-to-one relationship with the plurality of optical fiber bundles; a plurality of cameras in a one-to-one relationship with the plurality of optical fiber bundles, each respective optical fiber bundle, of the plurality of optical fiber bundles, having a respective lens, of the plurality of lenses, located at a respective distal end, and a camera, of the plurality of cameras, located at a respective proximal end, the plurality of optical fiber bundles being coupled together at a common distal end, and otherwise being uncoupled from one another, a bending radius of the endoscope defined by a largest respective bending radius of each of the plurality of optical fiber bundles; and a controller configured to: receive respective images from each of the plurality of cameras, receiving, at the controller, the respective images from each of the plurality of cameras; combining, at the controller, the respective images into a single higher resolution image; and combining the respective images into a depth-map of objects in front of the plurality of lenses.

The method further comprises: removing, at the controller, dead pixels from the respective images prior to combining the respective images into one or more of the single higher resolution image and the depth-map. The method further comprises: combining the respective images into the depth-map using a light field processing. Two or more of the plurality of lenses have one or more of: different depths of field, different fields of view of objects in front of the plurality of lenses: and different angular views of objects in front of the plurality of lenses.

In accordance with an embodiment of the present disclosure, an endoscope apparatus comprises: a plurality of optical fiber bundles; a plurality of lenses in a one-to-one correspondence with the plurality of optical fiber bundles, each lens of the plurality of lenses comprising a distinct depth of field and a distinct angle of view in relation to another lens of the plurality of lenses; and a plurality of cameras in a one-to-one correspondence with the plurality of optical fiber bundles.

In accordance with an embodiment of the present disclosure, a method of providing an endoscope apparatus comprises: providing a plurality of optical fiber bundles; providing a plurality of lenses in a one-to-one correspondence with the plurality of optical fiber bundles, providing the plurality of lenses comprising providing each lens of the plurality of lenses with a distinct depth of field and a distinct angle of view in relation to another lens of the plurality of lenses; and providing a plurality of cameras in a one-to-one correspondence with the plurality of optical fiber bundles.

In accordance with an embodiment of the present disclosure, a method of imaging, by way of an endoscope apparatus, comprises: providing the apparatus, providing the apparatus comprising: providing a plurality of optical fiber bundles; providing a plurality of lenses in a one-to-one correspondence with the plurality of optical fiber bundles, providing the plurality of lenses comprising providing each lens of the plurality of lenses with a distinct depth of field and a distinct angle of view in relation to another lens of the plurality of lenses; and providing a plurality of cameras in a one-to-one correspondence with the plurality of optical fiber bundles; and operating the apparatus by way of a controller.

Yet a further aspect of the present disclosure provides a computer-readable medium storing a computer program, wherein execution of the computer program is for: at an endoscope having: a plurality of optical fiber bundles; a plurality of lenses in a one-to-one relationship with the plurality of optical fiber bundles; a plurality of cameras in a one-to-one relationship with the plurality of optical fiber bundles, each respective optical fiber bundle, of the plurality of optical fiber bundles, having a respective lens, of the plurality of lenses, located at a respective distal end, and a camera, of the plurality of cameras, located at a respective proximal end, the plurality of optical fiber bundles being coupled together at a common distal end, and otherwise being uncoupled from one another, a bending radius of the endoscope defined by a largest respective bending radius of each of the plurality of optical fiber bundles; and a controller configured to: receive respective images from each of the plurality of cameras, receiving, at the controller, the respective images from each of the plurality of cameras; combining, at the controller, the respective images into a single higher resolution image; and combining the respective images into a depth-map of objects in front of the plurality of lenses. The computer-readable medium comprises a non-transitory computer-readable medium.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

Various implementations and aspects of the present disclosure will be described with reference to the below details. The following description and drawings are illustrative of the present disclosure and are not to be construed as limiting the present disclosure. Numerous specific details are described to provide a thorough understanding of various implementations of the present disclosure. However, in certain instances, well-known or conventional details are not described in order to provide a concise discussion of implementations of the present disclosure.

The systems and methods described herein may be useful in the field of neurosurgery, including oncological care, neurodegenerative disease, stroke, brain trauma, and orthopedic surgery; however, extending these concepts to other conditions or fields of medicine is also encompassed by the present disclosure. The surgical process is applicable to surgical procedures for brain, spine, knee and any other suitable region of the body.

Various apparatuses and processes are below described to provide examples of implementations of the disclosed herein system. No implementation below described limits any claimed implementation and any claimed implementations may cover processes or apparatuses that differ from those below described. The claimed implementations are not limited to apparatuses or processes having all of the features of any one apparatus or process below described or to features common to multiple or all of the apparatuses or processes below described. It is possible that an apparatus or process described below is not an implementation of any claimed subject matter.

Furthermore, numerous specific details are set forth in order to provide a thorough understanding of the implementations herein described. However, the implementations described herein may be practiced without these specific details. In other instances, well-known methods, procedures and components have not been described in detail so as not to obscure the implementations described herein.

As used herein, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

For the purpose of this present disclosure, language of "at least one of X, Y, and Z" and "one or more of X, Y and Z" may be construed as X only, Y only, Z only, or any combination of two or more items X, Y, and Z, e.g., XYZ, XY, YZ, ZZ, and the like. Similar logic may be applied for two or more items in any occurrence of "at least one . . . " and "one or more . . . " language.

Figure 1:
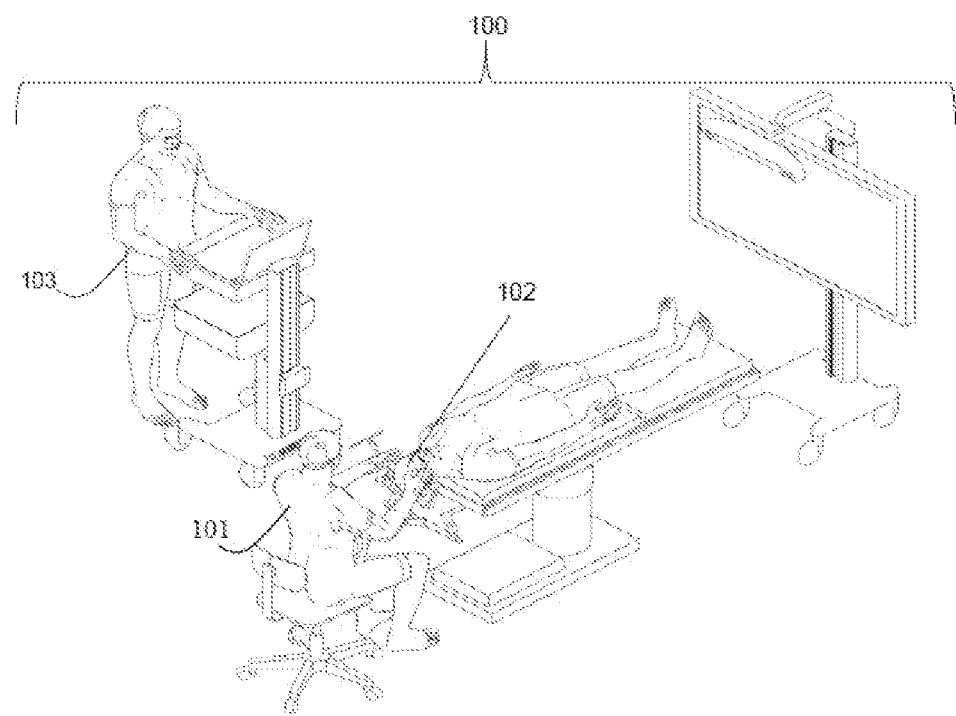
FIG. 1 is a diagram illustrating an operating room set up for a minimally invasive access port-based medical procedure, in accordance with an embodiment of the present disclosure.

Referring to FIG. 1, this diagram illustrates a navigation system 100 is shown to support minimally invasive access port-based surgery, in accordance with an embodiment of the present disclosure. A neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
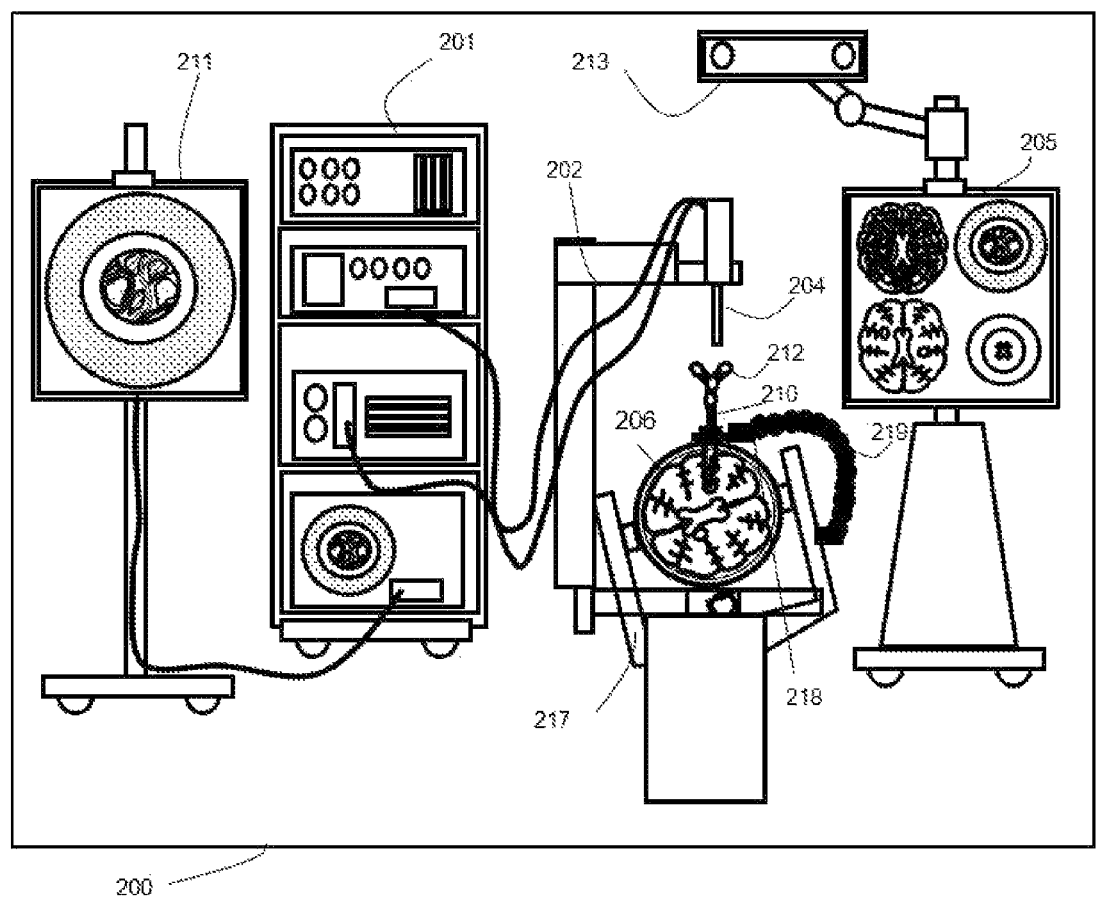
FIG. 2 is a diagram illustrating components of a medical navigation system that may be used to implement a surgical plan for a minimally invasive surgical procedure, in accordance with an embodiment of the present disclosure.

Referring to FIG. 2, this diagram illustrates components of an example medical navigation system 200, according to embodiments of the present disclosure. The medical navigation system 200 illustrates a context in which a surgical plan including equipment, e.g., tool and material, tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 is mounted on a frame, e.g., a rack or cart, and may contain a computer or controller (examples provided with reference to FIGS. 3 and 6), planning software, navigation software, a power supply, software to manage the mechanical arm 202, and tracked instruments. In one example non-limiting implementation, the equipment tower 201 comprises a single tower configuration with dual display monitors 211, 205, however other configurations may also exist, e.g., dual tower, single display, etc. Furthermore, the equipment tower 201 is configured with a universal power supply (UPS) to provide emergency power, in addition to a regular AC adapter power supply.

Still referring to FIG. 2, a patient's anatomy may be held in place by a holder. For example, in a neurosurgical procedure, the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as below described in more detail. In one example, the tracking camera 213 comprises a 3D (three-dimensional) optical tracking stereo camera, similar to one made by Northern Digital Imaging (NDI®), configured to locate reflective sphere tracking markers 212 in 3D space.

Still referring to FIG. 2, in another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example, the introducer 210 and associated pointing tools. Tracking markers may also placed on surgical tools or materials to be tracked. The secondary display 205 may provide output of the tracking camera 213. In one example non-limiting implementation, the output may be shown in axial, sagittal, and coronal views as part of a multi-view display. The introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

Still referring to FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down, e.g., along the longitudinal axis of the access port 206, relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point, e.g., on another patient support, such as on the surgical bed, to ensure that when locked in place, the guide clamp 218 does not move relative to the patient's head.

Figure 3:
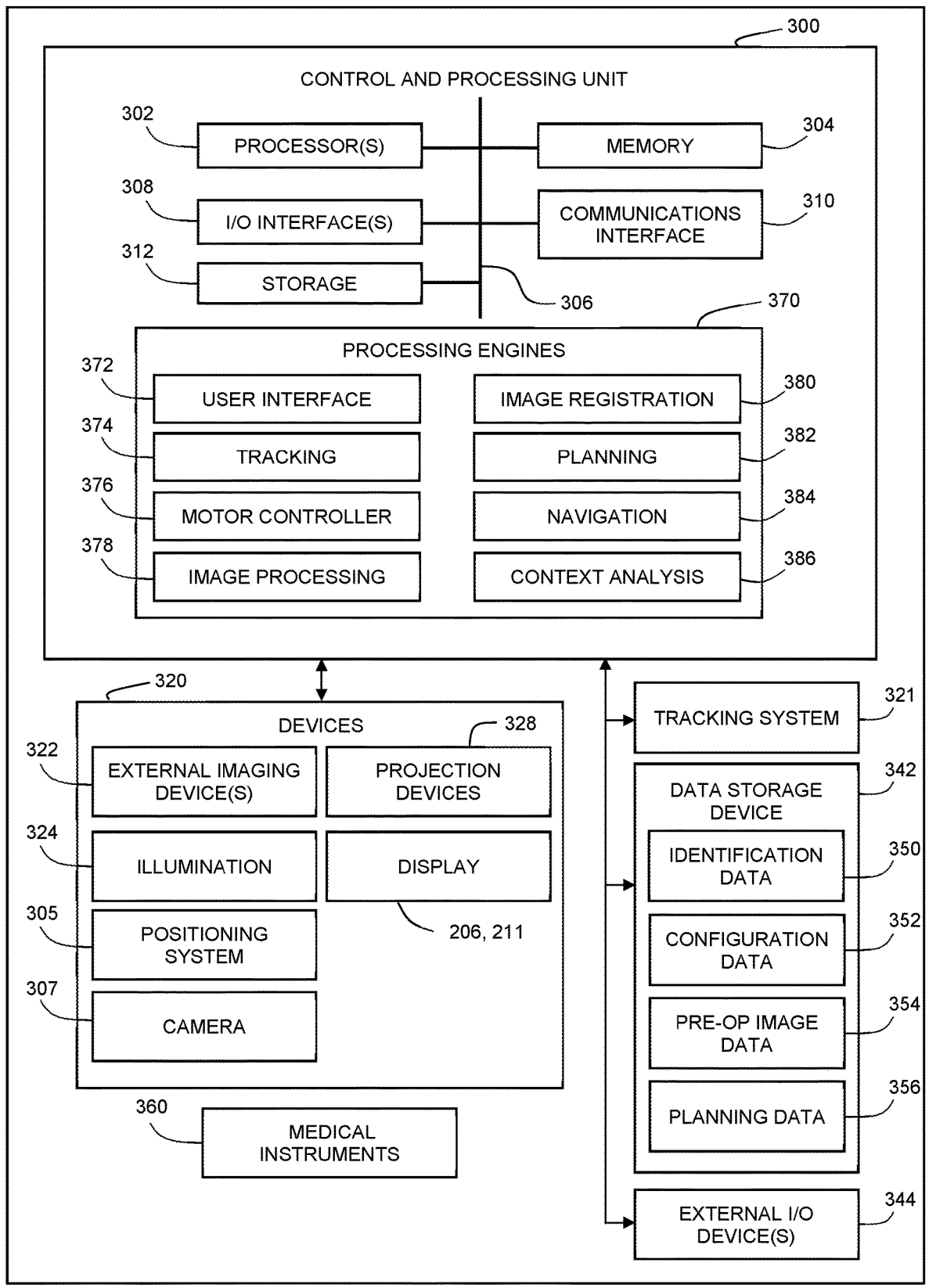
FIG. 3 is a block diagram illustrating components of a planning system used to plan a medical procedure that may then be implemented using the navigation system, as shown in FIG. 2, in accordance with an embodiment of the present disclosure.

Referring to FIG. 3, a block diagram is shown illustrating a control and processing unit 300 that may be used in the navigation system 200, as shown in FIG. 2, e.g., as part of the equipment tower, in accordance with an embodiment of the present disclosure. In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 is interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device, e.g., a computer, hard drive, digital media device, and/or server, having a database stored thereon.

Still referring to FIG. 3, the data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Still referring to FIG. 3, the medical instruments 360 may be identifiable using control and processing unit 300. Medical instruments 360 may be connected to and controlled by control and processing unit 300, and/or medical instruments 360 may be operated and/or otherwise employed independently of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Still referring to FIG. 3, the control and processing unit 300 may also interface with a number of configurable devices and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Still referring to FIG. 3, aspects of the present disclosure may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately, in one example non-limiting implementation the processing modules 370 may be stored in the memory 304 and the processing modules may be collectively referred to as processing modules 370.

Still referring to FIG. 3, the system is not intended to be limited to the components as shown. One or more components of the control and processing unit 300 may be provided as an external component or device. In one example non-limiting implementation, navigation engine 384 may be provided as an external navigation system that is integrated with control and processing unit 300.

Still referring to FIG. 3, some implementations may be implemented using processor 302 without additional instructions stored in memory 304. Some implementations may be implemented using the instructions stored in memory 304 for execution by one or more general purpose microprocessors. Thus, the present disclosure is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, non-volatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc., among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumors and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to other suitable medical procedures.

Figure 4:
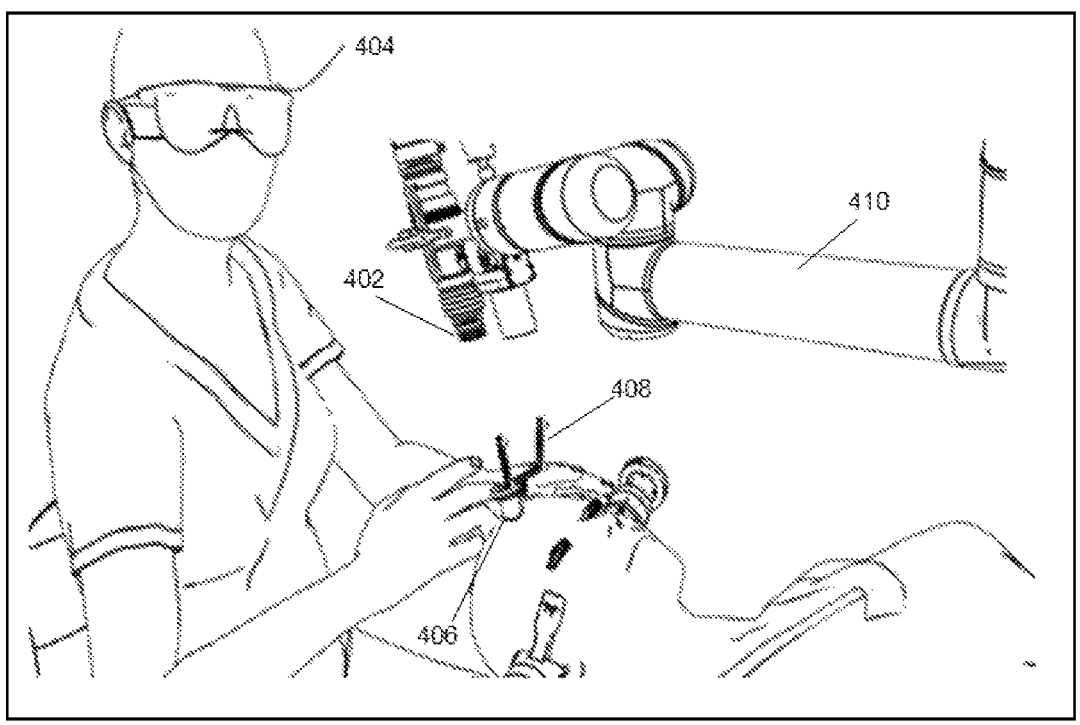
FIG. 4 is a diagram illustrating a port-based brain surgery using a video scope, in accordance with an embodiment of the present disclosure.

Referring to FIG. 4, this diagram illustrates a port-based brain surgery procedure using a video scope, in accordance with an embodiment of the present disclosure. An operator 404, for example, a surgeon, may align video scope 402 to peer down port 406. Video scope 402 is attached to an adjustable mechanical arm 410. Port 406 may have a tracking tool 408 attached to it where tracking tool 408 is tracked by a tracking camera of a navigation system. Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
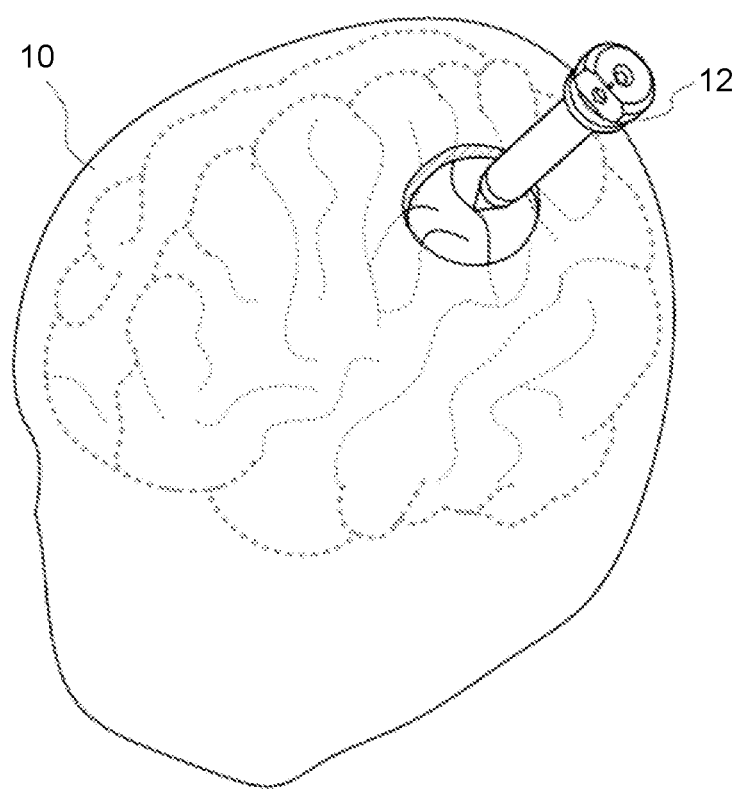
FIG. 5 is a diagram illustrating insertion of an access port into a human brain, for providing access to interior brain tissue during a medical procedure, in accordance with an embodiment of the present disclosure.

Referring to FIG. 5, this diagram illustrates the insertion of an access port 12 into a human brain 10, in order to provide access to interior brain tissue during a medical procedure, in accordance with an embodiment of the present disclosure. The access port 12 is inserted into a human brain 10, providing access to interior brain tissue. Access port 12 may include, but is not limited to, instruments such as catheters, surgical probes, and/or cylindrical ports such as the NICO BrainPath®. Surgical tools and instruments may then be inserted within a lumen of the access port 12 in order to perform surgical, diagnostic or therapeutic procedures, such as resecting tumors as necessary. However, the present disclosure applies equally well to catheters, DBS needles, a biopsy procedure, and also to biopsies and/or catheters in other medical procedures performed on other parts of the body. In the example of a port-based surgery, a straight and/or linear access port 12 is typically guided down a sulci path of the brain. Surgical instruments and/or surgical tools would then be inserted down the access port 12.

Figure 6:
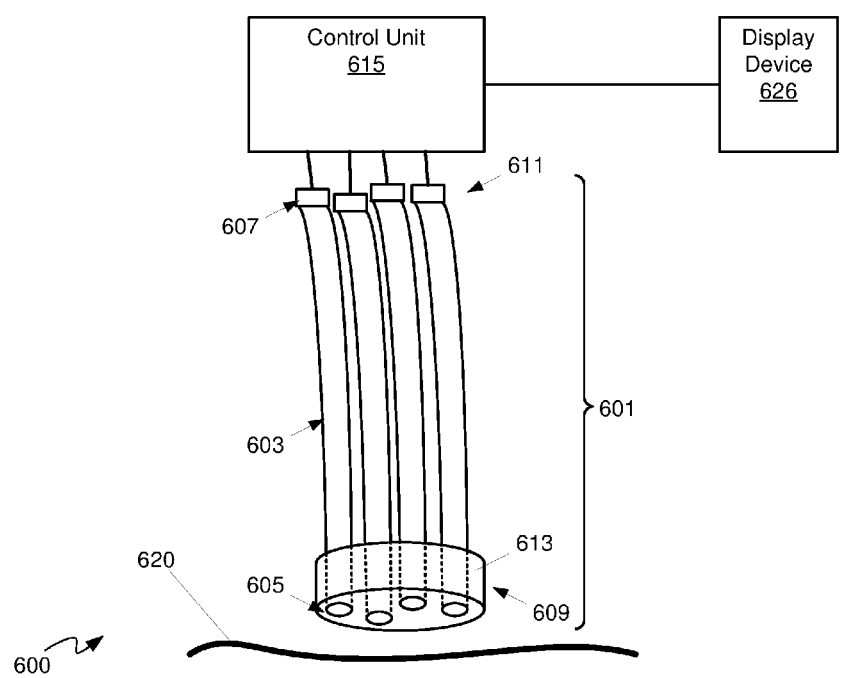
FIG. 6 is a schematic diagram illustrating a system that includes a flexible high-resolution endoscope, in accordance with an embodiment of the present disclosure.

Referring to FIG. 6, this schematic diagram illustrates a system 600 comprising a flexible high-resolution endoscope 601 that could be used with access port 12, in accordance with an embodiment of the present disclosure. Elements of system 600 are not drawn to scale, but are depicted schematically to show functionality. Endoscope 601 comprises: a plurality of optical fiber bundles 603; a plurality of lenses 605 in a one-to-one relationship with plurality of optical fiber bundles 603; and, a plurality of cameras 607 in a one-to-one relationship with the plurality of optical fiber bundles 603, each respective optical fiber bundle 603, of the plurality of optical fiber bundles 603, having a respective lens 605, of the plurality of lenses 605, located at a respective distal end 609, and a camera 607, of the plurality of cameras 607, located at a respective proximal end 611, plurality of optical fiber bundles 603 being coupled together at a common distal end 609, and otherwise being uncoupled from one another, a bending radius of endoscope 601 defined by a largest respective bending radius of each of the plurality of optical fiber bundles 603. The plurality of lenses 605 are each formed in a common optical element 613 located at common distal end 609, which also couples together plurality of optical fiber bundles 603 at common distal end 609. Respective distal ends 609 of each optical fiber bundle 603 are coincident with common distal end 609, such each of distal ends 609 and common distal end 609 are similarly numbered.

Still referring to FIG. 6, the system 600 further comprises a controller 615, coupled with each of cameras 607, and a display device 626, as below described in more detail. In general, endoscope 601 is configured to acquire a plurality of images of a tissue sample 620, which can include, but is not limited to, a tissue sample accessible via access port 12. In particular, respective distal ends 609 of the plurality of optical fiber bundles 603, and respective lenses 605 located at respective distal ends 609, are spaced apart from one another to provide different views of objects (such as tissue sample 620) in front of the respective distal ends 609. In some of these implementations, endoscope 601 can thereby form a plenoptic camera.

Still referring to FIG. 6, while only one of each of plurality of optical fiber bundles 603, plurality of lenses 605, and plurality of cameras 607, the endoscope 601 comprises four optical fiber bundles 603, four respective lenses 605 and four respective cameras 607. However, endoscope 601 comprises as few as two of each of optical fiber bundles 603, lenses 605 and cameras 607, and comprises more than four of each of optical fiber bundles 603, lenses 605 and cameras 607. However, at a minimum, endoscope 601 comprises the plurality of optical fiber bundles comprises a first optical fiber bundle 603 and a second optical fiber bundle 603, each having the respective lens 605 located at the respective distal end 609, and the respective camera 607 located at the respective proximal end 611, which can thereby form a three-dimensional camera.

Still referring to FIG. 6, each optical fiber bundle 603 comprises an optical fiber having a respective diameter of are less than or equal to about 2 mm (however, optical fiber bundles 603 need not have all the same diameter). In particular, each optical fiber bundle 603 can have a diameter that can convey images from respective lenses 605 to respective cameras 607 with resolutions similar to cameras 607. For example, 2 mm optical fiber bundles can convey images of resolutions of about 18 kilopixels, and hence cameras 607 can produce digital images have resolutions of about 18 kilopixels.

Still referring to FIG. 6, furthermore, as each optical fiber bundle 603 is free to bend independent from every other optical fiber bundle 603, other than at common distal end 609, the bending radius of endoscope 601 is determined and/or defined by the individual bending radii of each optical fiber bundle 603 rather than a total bending radii if optical fiber bundles 603 were coupled together along their entire length. Put another way, a bending radius of endoscope 601 is defined by a largest respective bending radius of each of the plurality of optical fiber bundles 603. As such, optical fiber bundles 603 of any suitable diameter are within the scope of present implementations; for example, a specified bending radius of endoscope 601 is used to select individual optical fibers that will meet this present disclosure, rather than selecting optical fibers that, when coupled together, will meet this present disclosure.

Still referring to FIG. 6, in other words, a plurality of optical fiber bundles 603 are coupled together at common distal end 609, e.g., by way of common optical element 613, and are otherwise uncoupled from one another. Indeed, each of plurality of optical fiber bundles 603 can bend from common distal end 609 independent of the other optical fiber bundles 603. As such plurality of optical fiber bundles 603 are not attached to each other than at common distal end 609.

Still referring to FIG. 6, each optical fiber bundle 603 can have a length that is commensurate with insertion through an access port (including, but not limited to, access port 12), as well as port-based surgery, such that common distal end 609 is inserted through an access port, and optical fiber bundles 603 join respective lenses 605 to respective cameras 607 such that cameras 607 do not block surgical access to access port 12, e.g., cameras 607 do not block access of a surgeon (and the like) and/or surgical tools (and the like) to access port 12. For example, each optical fiber bundle 603 can be greater than about a half meter long. Furthermore, optical fiber bundles 603 need not all be the same length, and some optical fiber bundles 603 can be longer or shorter than other optical fiber bundles 603.

Still referring to FIG. 6, each lens 605 is formed in common optical element 613 located at common distal end 609. Common optical element 613 comprises one or more of optical glass and optical plastic, at least at a tissue facing side of common optical element 613. Each lens 605 is formed in the common optical element 613 using, for example, laser processing (including, but not limited to, femtosecond laser processing, and the like) to form profiles in the index of refraction in the glass and/or plastic of common optical element 613 which correspond to each lens 605. However, lenses 605 can also be tiled together using one or more of a mechanical assembly, adhesives, and the like.

Still referring to FIG. 6, two or more of plurality of lenses 605 can have one or more of: different depths of field, different fields of view of objects in front of the plurality of lenses 605: and different angular views of objects in front of the plurality of lenses 605. Hence, when endoscope 601 is imaging tissue sample 620, tissue sample 620 can be imaged using at least two different depths of field and/or at least two different fields of view and/or at least two different angular views.

Still referring to FIG. 6, each camera 607 can include, but is not limited to one or more of a charge-coupled device (CCD) camera, a digital camera, an optical camera, and the like, and is generally configured to acquire digital images, and in particular digital images received from a respective lens 605 via a respective optical fiber bundle 603. While not depicted, each camera 607 can further include one or more respective lenses for focusing light from a respective optical fiber 603 onto a respective imaging element (such as a CCD). While not depicted, endoscope 601 can include one or more devices for coupling optical fiber bundles 603 to a respective camera 607. Furthermore, each camera 607 can have a resolution of about 18 kilopixels.

Still referring to FIG. 6, the controller 615 comprises any suitable combination of computing devices, processors, memory devices and the like. In particular, controller 615 comprises one or more of a data acquisition unit, configured to acquire data and/or images at least from cameras 607, and an image processing unit, configured to process data and/or images from cameras 607 for rendering at display device 626. Hence, controller 615 is interconnected with cameras 607 and display device 626. In some implementations, controller 615 comprises control and processing unit 300, as shown in FIG. 3, and/or controller 615 communicates with control and processing unit 300, as shown in FIG. 3, and/or controller 615 can be under control of communication with control and processing unit 300, as shown in FIG. 3.

Still referring to FIG. 6, in some implementations, however, controller 615 can be a component of endoscope 601 such that endoscope 601 comprises controller 615. In these implementations, endoscope 601 can be provided as a unit with controller 615 which can be interfaced with control and processing unit 300 depicted in FIG. 3, and the like. The display device 626 comprises any suitable display device including, but not limited to, cathode ray tubes, flat panel displays, and the like. For example, display device 626 comprises one or more of monitors 205, 211, as shown in FIG. 2, and/or displays 305, 311 shown in FIG. 3.

Figure 7:
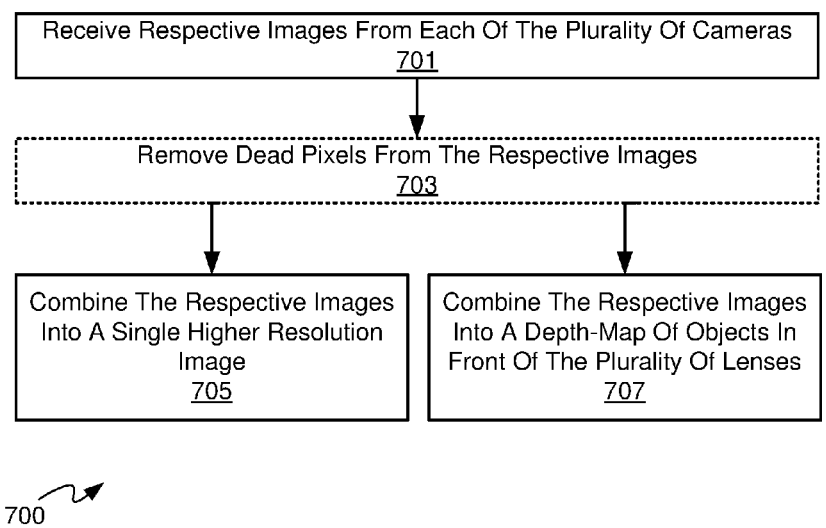
FIG. 7 is a flow diagram illustrating a method for combining images using the flexible high-resolution endoscope, as shown in FIG. 6, in accordance with an embodiment of the present disclosure.

Referring to FIG. 7, this flow diagram illustrates a method 700 for combining images from cameras, according to non-limiting implementations, in accordance with an embodiment of the present disclosure. In order to assist in the explanation of method 700, assumed is that method 700 is performed using system 600, and specifically by controller 615. Indeed, the method 700 is one way in which system 600 and/or controller 615 can be configured. Furthermore, the following discussion of method 700 will lead to a further understanding of controller 615, and system 600 and its various components. However, the system 600 and/or controller 615 and/or method 700 can be varied, and need not work exactly as discussed herein in conjunction with each other, and that such variations are within the scope of present disclosure.

Still referring to FIG. 7, regardless, the method 700 need not be performed in the exact sequence as shown, unless otherwise indicated; and likewise various blocks are performed in parallel rather than in sequence; hence the elements of method 700 are referred to herein as "blocks" rather than "steps". The method 700 can be implemented on variations of system 600 as well. At block 701, controller 615 receives respective images from each of plurality of cameras 607. At an optional block 703 (indicated by block 703 being shown in broken lines), controller 615 removes dead pixels from the respective images. In some implementations, block 703 is not performed. Furthermore, in other implementations, when no dead pixels are in the respective images, block 703 is not performed. At block 705, controller 615 can combine the respective images into a single higher resolution image. At block 707, controller 615 can combine the respective images into a depth-map of objects in front of the plurality of lenses 605 using, for example, light field processing techniques, and the like. In some implementations, controller 615 can implement both blocks 705, 707, for example, in parallel with each other and/or one after the other. In other implementations, controller 615 can implement one of blocks 705, 707. In some implementations, controller 615 can implement blocks 703 in conjunction with one or more of blocks 705, 707.

Figure 8:
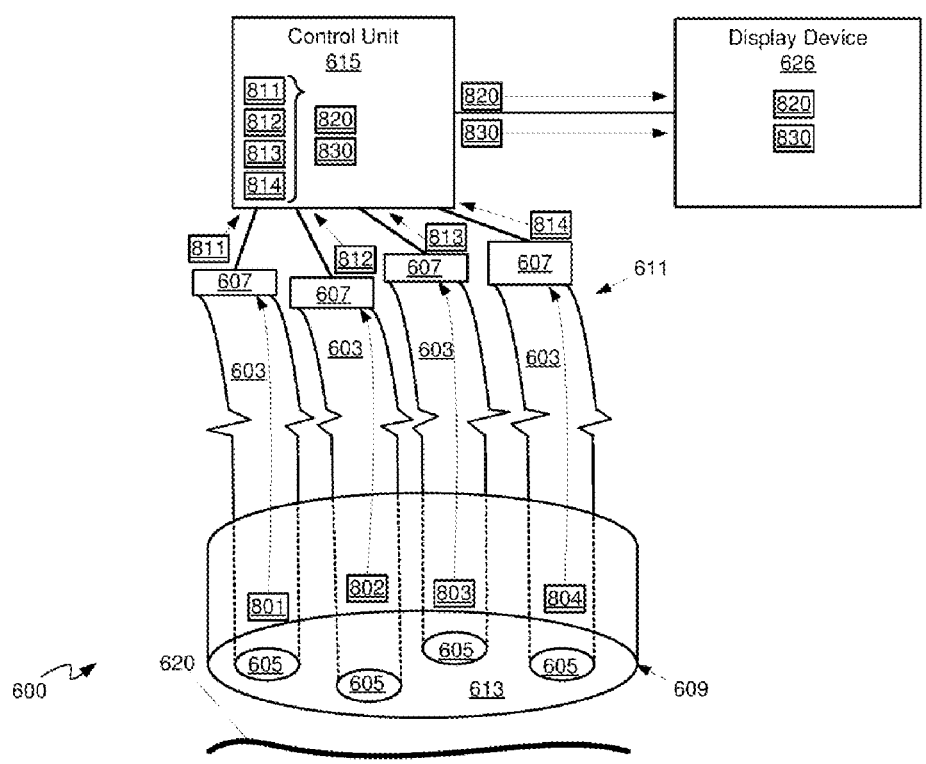
FIG. 8 is a diagram illustrating the system, as shown in FIG. 6, in use, in accordance with an embodiment of the present disclosure.

Still referring to FIG. 7, back to FIG. 6, and ahead to FIG. 8, the method 700, respective distal ends 609 and respective proximal ends 611 are enlarged, and the entire length of each optical fiber bundle 603 is not depicted. In FIG. 8, light 801, 802, 803, 804 representing different respective views of tissue sample 620 is collected by respective lenses 601 and conveyed to respective cameras 607 by respective optical fiber bundles 603. Cameras 607 convert light 801, 802, 803, 804 into respective digital images 811, 812, 813, 814 of tissue sample 620, which are received at controller 615, e.g. at block 701 of method 700.

Still referring to FIG. 7, back to FIG. 6, and ahead to FIG. 8, the controller 615 processes digital images 811, 812, 813, 814 to optionally remove dead pixels in each of digital images 811, 812, 813, 814, e.g., at block 703 of method 700, and combine digital images 811, 812, 813, 814 into one or more of single higher resolution image 820 of tissue sample 620, e.g., at block 705 of method 700, and a depth-map 830 of tissue sample 620, e.g., at block 707 of method 700. Controller 615 can be configured to produce higher resolution image 820 and/or depth-map 830 from digital images 811, 812, 813, 814 using light field processing. Controller 615 can then provide higher resolution image 820 and/or depth-map 830 to display device 626 for rendering thereupon. Controller can optionally provide one or more of digital images 811, 812, 813, 814 to display device 626 for rendering thereupon (not depicted).

Still referring to FIG. 7, back to FIG. 6, and ahead to FIG. 8, dead pixels of digital images 811, 812, 813, 814 and pixels of digital images 811, 812, 813, 814 can be combined and/or interlaced and/or used to produce interpolated pixels to produce image 820 which has a higher resolution of each of digital images 811, 812, 813, 814 taken alone. Hence, if each of digital images 811, 812, 813, 814 has a resolution of about 18 kilopixels, image 820 can have a resolution can at least about double 18 kilopixels. Thus, endoscope 601 is configured to images having resolutions similar to those produced by existing high-resolution endoscopes, but without the attendant problems with bending radius suffered by those existing high-resolution endoscopes. Using light field processing of the separate digital images 811, 812, 813, 814 from cameras 607, a depth-map of tissue sample 620 (or any other object) imaged by lenses 605 can be reconstructed, which can allow structures with differing depth to be more easily detected and/or see. When endoscope 601 is configured for omni-focusing (having all objects imaged by lenses 605 in focus), selective post-acquisition focusing, and depth of field control can be possible, both in post-acquisition and real-time. This post-processing can also allow for removal of dead pixels which can be caused by broken fibers within fiber bundles without significant loss of detail. In other words, block 703 can be performed in conjunction with either of blocks 705, 707.

Still referring to FIG. 7, back to FIG. 6, and ahead to FIG. 8, in some implementations, two or more of digital images 811, 812, 813, 814 can be combined into a stereo image of tissue sample 620. Indeed, a plurality of pairs of digital images 811, 812, 813, 814 can be combined to produce a plurality of stereo images of tissue sample 620, for example from different angles and/or different fields of view and/or different depths of field. In yet further implementations, where lenses 605 have different depths of field, but a similar field of view, digital images 811, 812, 813, 814 can be combined into a plenoptic image of tissue sample 620 such that a depth of field of the plenoptic image can be selected by a user interacting with controller 615, display device 626 and an input device (not depicted). Indeed, in these implementations, lenses 605 can be configured for omni-focusing, where all objects, e.g., including, but not limited to tissue sample 620, imaged by lenses 605 are in focus; while each individual lens 605 may not have all objects in focus, collectively lenses 605 can image all objects in focus such that, collectively, all images produced by cameras 607 include all objects imaged by lenses 605 in focus, at least in one of the images.

Figure 9:
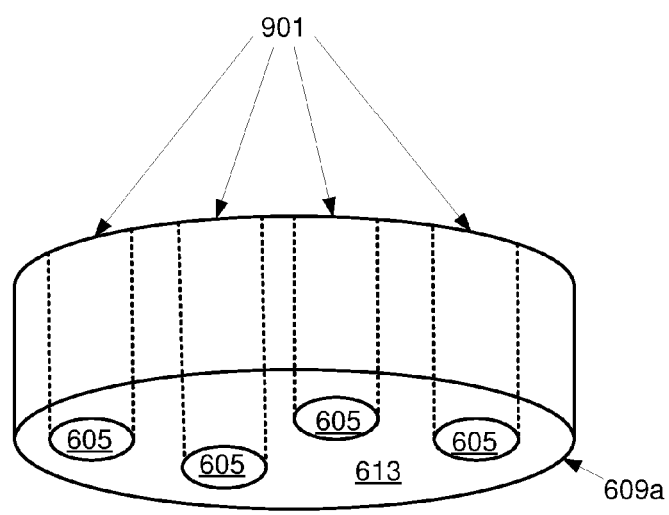
FIG. 9 is a diagram illustrating an optical element of the flexible high-resolution endoscope, as shown in FIG. 6, in accordance with an embodiment of the present disclosure.

Referring to FIG. 9, this diagram illustrates a common optical element 613. Common optical element 613 is generally configured to both provide lenses 605 and couple together the plurality of optical fiber bundles 603 at common distal end 609, in accordance with an embodiment of the present disclosure. Hence, common optical element 613 comprises lenses 605 and, as depicted, respective slots 901 for receiving a respective optical fiber bundle 603 on a proximal side, each slot 901 in a body of common optical element 613, and each slot 901 terminating at a respective lens 605 at distal end 609. Hence, each slot 901 has a diameter that is similar to a diameter of a respective optical fiber bundle 603 such that each slot 901 can receive a respective optical fiber bundle 603 and seat a distal end of each respective optical fiber bundle 603 at a respective lens 605. While not depicted, common optical element 613 can further comprise a mechanism for fixing each respective optical fiber bundle 603 within a respective slot 901; alternatively, adhesives (including, but not limited to optical adhesives) can be used to fix a respective optical fiber bundle 603 within a respective slot 901.

Figure 10:
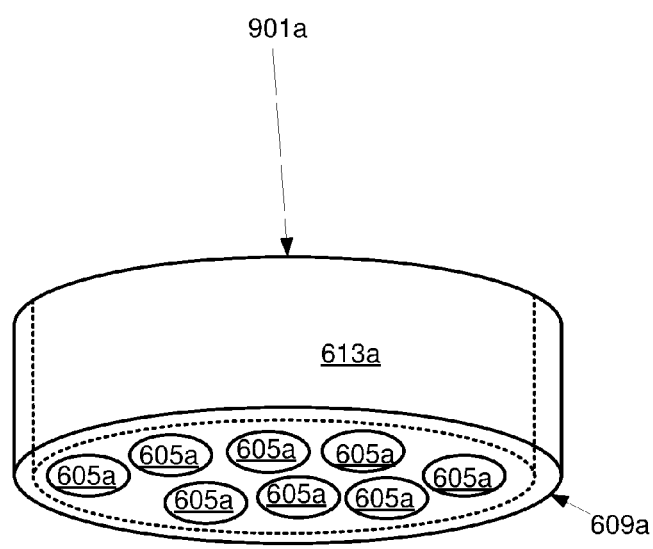
FIG. 10 is a diagram illustrating an optical element that can be used with the flexible high-resolution endoscope, as shown in FIG. 6, in accordance with an embodiment of the present disclosure.

Referring to FIG. 10, this diagram illustrates an optical element 613a, substantially similar to optical element 613, with like elements having like numbers, however with an "a" appended thereto, in accordance with an embodiment of the present disclosure. Hence, optical element 613a comprises a plurality of lenses 605a at a distal end 609a. However, in contrast to optical element 613, optical element 613a comprises eight lenses 605a, and one slot 901a configured to receive a plurality of optical fiber bundles. However, optical element 613a comprises fewer than eight lenses 605a and more than eight lenses 605a.

Figure 11:
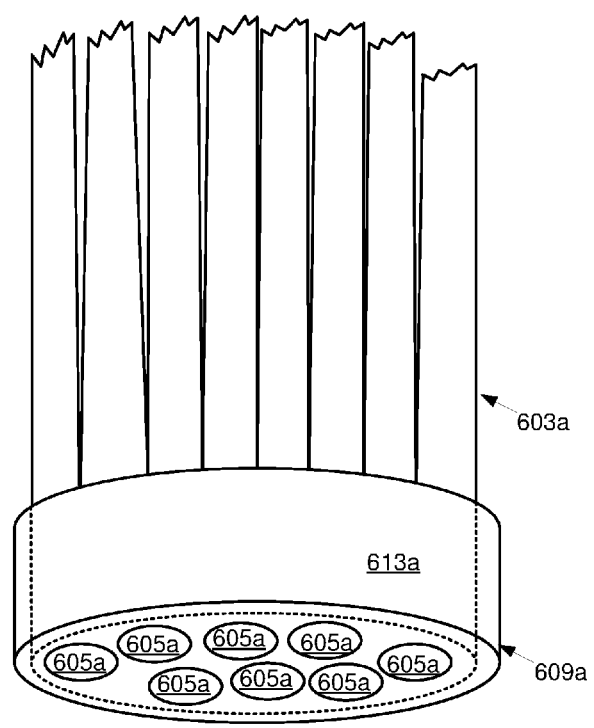
FIG. 11 is a diagram illustrating the optical element, as shown in FIG. 10, in accordance with an embodiment of the present disclosure.

Referring to FIG. 11, which depicts slot 901a of optical element 613a receiving a plurality of optical fiber bundles 603a, in a one-to-one relationship with plurality of lenses 605a, optical fiber bundles 603a being coupled together a common distal end 609a, and otherwise being uncoupled from one another, in accordance with an embodiment of the present disclosure. While only a portion of optical fiber bundles 603a is depicted, it is assumed that each optical fiber bundle 603a is coupled to a respective camera at a proximal end, similar to implementations depicted in FIG. 6. In particular, coupling together of optical fiber bundles 603a at common distal end 609a results in a total diameter of coupled optical fiber bundles 603a that is about a same diameter as slot 901a. While not depicted, distal ends of optical fiber bundles 603a are aligned with a respective lens 605a, as in system 600. For example, a geometry of distal ends of optical fiber bundles 603a can be selected so that when distal ends of optical fiber bundles 603a are coupled together, they form a geometric pattern, and lenses 605a can be arranged into a similar pattern. Hence, when distal ends of optical fiber bundles 603a are inserted into slot 901a, one or more of distal ends of optical fiber bundles 603a and common optical element 613a can be rotated until alignment with lenses 605a occurs. Such alignment can be determined by one or more of processing and viewing images from cameras to which each optical fiber bundle 603a is coupled.

Still referring to FIG. 11, alternatively, distal ends of optical fiber bundles 603a can have a cross-section of a given geometric shape, for example, a geometric shape having at least one flat side, and a respective cross-section slot 901a can have a similar shape; hence, when distal ends of optical fiber bundles 603a are inserted into slot 901a the flat sides align which can cause the distal ends of optical fiber bundles 603a to align with lenses 605a. Alternatively, a mechanical assembly can be used to couple together distal ends of optical fiber bundles 603a and further space distal ends of optical fiber bundles 603a in a pattern similar to lenses 605a; in these implementations, slot 901a can be adapted to receive the distal ends of optical fiber bundles 603a and the mechanical assembly.

Figure 12:
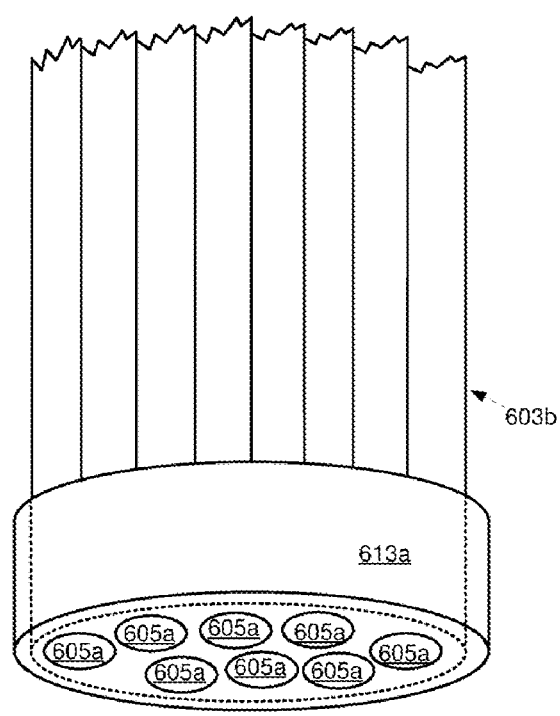
FIG. 12 is a diagram illustrating the optical element, as shown in FIG. 10, in accordance with an embodiment of the present disclosure.

Referring to FIG. 12, which depicts common optical element 613a being used with an optical fiber bundle 603b having a similar diameter to that of slot 901a, and can include a plurality of optical fiber bundles coupled together at common distal end 609a, as well as along their length, in accordance with an embodiment of the present disclosure. Hence, optical fiber bundle 603b is configured to convey images from lenses 605a to one or more cameras at a common proximal end. Indeed, individual optical fiber bundles of optical fiber bundle 603b need not be aligned with lenses 605a as a proximal end of optical fiber bundle 603b can have a diameter that can receive light from all of lenses 605a. The bending radius of optical fiber bundle 603b is larger than a bending radius of endoscope 601, however such difference in bending radius does not preclude use of common optical element 613a with more typical endoscopes.

Figure 13:
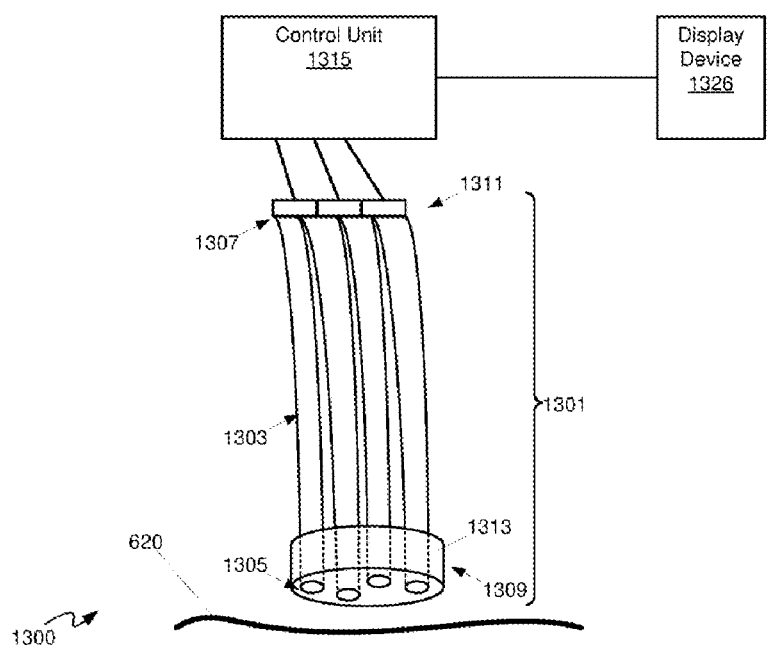
FIG. 13 is a schematic diagram illustrating a system comprising an alternative flexible high-resolution endoscope, in accordance with an embodiment of the present disclosure.

Referring to FIG. 13, which depicts an alternative system 1300 that includes an example of a flexible high-resolution endoscope 1301 that could be used with access port 12 to image tissue sample 620, in accordance with an embodiment of the present disclosure. System 1300 is substantially similar to system 600, with like elements having like numbers, but in a "1300" series rather than a "600" series. However, in contrast to endoscope 601, optical fiber bundles of endoscope 1301 are coupled together at both a common distal end and a common proximal end, and are otherwise uncoupled, and cameras used with endoscope 1301 are not necessarily in a one-to-one relationship with the optical fiber bundles.

Still referring to FIG. 13, hence, endoscope 1301 comprises: a plurality of optical fiber bundles 1303; a plurality of lenses 1305 in a one-to-one relationship with plurality of optical fiber bundles 1303; and, one or more cameras 1307. Each respective optical fiber bundle 1303, of the plurality of optical fiber bundles 1303, has a respective lens 1305, of the plurality of lenses 1305, located at a respective distal end 1309. One or more cameras 1307 are located at a common proximal end 1311 of the plurality of optical fiber bundles 1303. Plurality of optical fiber bundles 1303 are coupled together at a common distal end 1309 and at common proximal end 1311, and are otherwise uncoupled from one another. As depicted, plurality of lenses 1305 are each formed in a common optical element 1313 similar to common optical element 613. As depicted, system 1300 further comprises a controller 1315, coupled to each of one or more cameras 1307, and a display device 1326.

Still referring to FIG. 13, while endoscope 1301, as depicted, includes three cameras 1307, in other implementations endoscope 1301 could include as few as one camera 1307 and more than three cameras 1307, including more than four cameras 1307. It is assumed, however, that cameras 1307 of endoscope 1301 are collectively configured to receive light from all of optical fiber bundles 1303, and that each of one or more cameras 1307 can be arranged to receive images from one or more of plurality of optical fiber bundles 1303. Hence, in these implementations, respective alignment of distal and proximal ends of optical fiber bundles 1303 with lenses 1305 and one or more cameras 1307 is less important than in system 600, as each of one or more cameras 1307 can be arranged to receive images from one or more of plurality of optical fiber bundles 1303. Controller 1315 can hence be configured to separate and/or combine images from each of one or more cameras 1307 into images corresponding to fields of view of each of lenses 1305.

Still referring to FIG. 13, indeed while, as depicted, each of distal ends of plurality of optical fiber bundles 1303 is aligned with a respective lens 1305, in other implementations, more than one of plurality of optical fiber bundles 1303 can be arranged to receive light from one or more of lenses 1305, such that plurality of optical fiber bundles 1303 functions optically as a larger optical fiber bundle similar to that depicted in FIG. 12. Indeed, in some implementations, common optical element 1313 can be replaced with common optical element 613a having one larger slot 901a instead of individual slots. However, as each of plurality of optical fiber bundles 1303 are free to bend individually, other than at ends 1309, 1311, a bending radius of endoscope 1301 is determined by the bending radii of individual optical fiber bundles 1303 rather than all of optical fiber bundles 1303 bending together.

Figure 14:
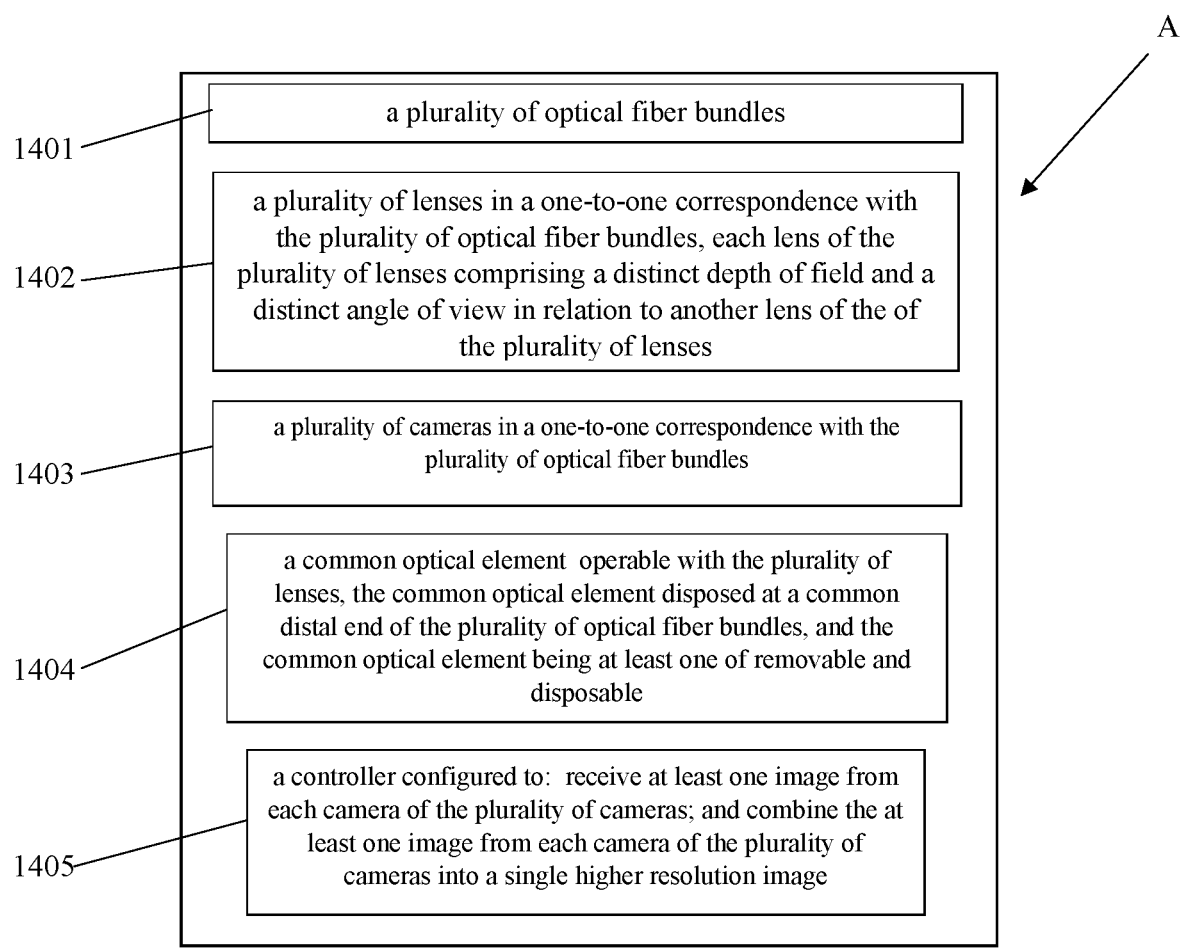
FIG. 14 is a block diagram illustrating an endoscope apparatus, in accordance with an embodiment of the present disclosure.

Referring to FIG. 14, this block diagram illustrates an endoscope apparatus A, in accordance with an embodiment of the present disclosure. The endoscope apparatus A comprises: a plurality of optical fiber bundles 1401; a plurality of lenses 1402 in a one-to-one correspondence with the plurality of optical fiber bundles 1401, each lens 1402 of the plurality of lenses 1402 comprising a distinct depth of field and a distinct angle of view in relation to another lens 1402 of the plurality of lenses 1402; and a plurality of cameras 1403 in a one-to-one correspondence with the plurality of optical fiber bundles 1402. The apparatus A further comprises a common optical element 1404 operable with the plurality of lenses 1402, the common optical element 1404 disposed at a common distal end of the plurality of optical fiber bundles 1402, and the common optical element 1404 being at least one of removable and disposable.

Still referring to FIG. 14, in the apparatus A, each lens 1402 of the plurality of lenses 1402 is disposed in the common optical element 1404. Each lens 1402 of the plurality of lenses 1402 is correspondingly disposed at a distal end of each optical fiber bundle 1401 of the plurality of optical fiber bundles 1401. Each camera 1403 of the plurality of cameras 1403 is correspondingly disposed at a proximal end of each optical fiber bundle 1401 of the plurality of optical fiber bundles 1401. The plurality of optical fiber bundles 1401 is coupled, together, at the common distal end. Each optical fiber bundle 1401 of the plurality of optical fiber bundles 1401 comprises a largest bending radius defining a largest bending radius of the apparatus A. The plurality of optical fiber bundles 1401 comprises a first optical fiber bundle and a second optical fiber bundle. The plurality of optical fiber bundles 1401, the plurality of lenses 1402, and the plurality of cameras 1403, together, forming a three-dimensional camera. Each optical fiber bundle distal end is spaced apart from another optical fiber bundle distal end; and each lens 1402 is spaced apart from another lens 1402 to provide a plurality of distinct views.

Still referring to FIG. 14, in the apparatus A, each lens of the plurality of lenses 1402 further comprises a distinct field of view in relation to another lens 1402 of the plurality of lenses 1402. The apparatus A further comprises a controller 1405 configured to: receive at least one image from each camera 1403 of the plurality of cameras 1403; and combine the at least one image from each camera 1403 of the plurality of cameras 1403 into a single higher resolution image. The controller 1405 is further configured to remove dead pixels from the at least one image from each camera 1403 of the plurality of cameras 1403. The controller 1405 is further configured to provide a depth map by combining the at least one image from each camera 1403 of the plurality of cameras 1403. The controller 1405 is further configured to provide the depth map by using light field processing. Each optical fiber bundle 1401 of the plurality of optical fiber bundles 1401 comprises a diameter in a range of up to approximately 2 mm. The common optical element 1404 comprises a body having a proximal end and a distal end, the distal end of the body configured to accommodate the plurality of lenses 1402, and the proximal end of the body comprising a plurality of slots configured to correspondingly receive the plurality of optical fiber bundles 1401, each slot of the plurality of slots correspondingly terminating at each lens of the plurality of lenses 1402 at the distal end of the body.

Figure 15:
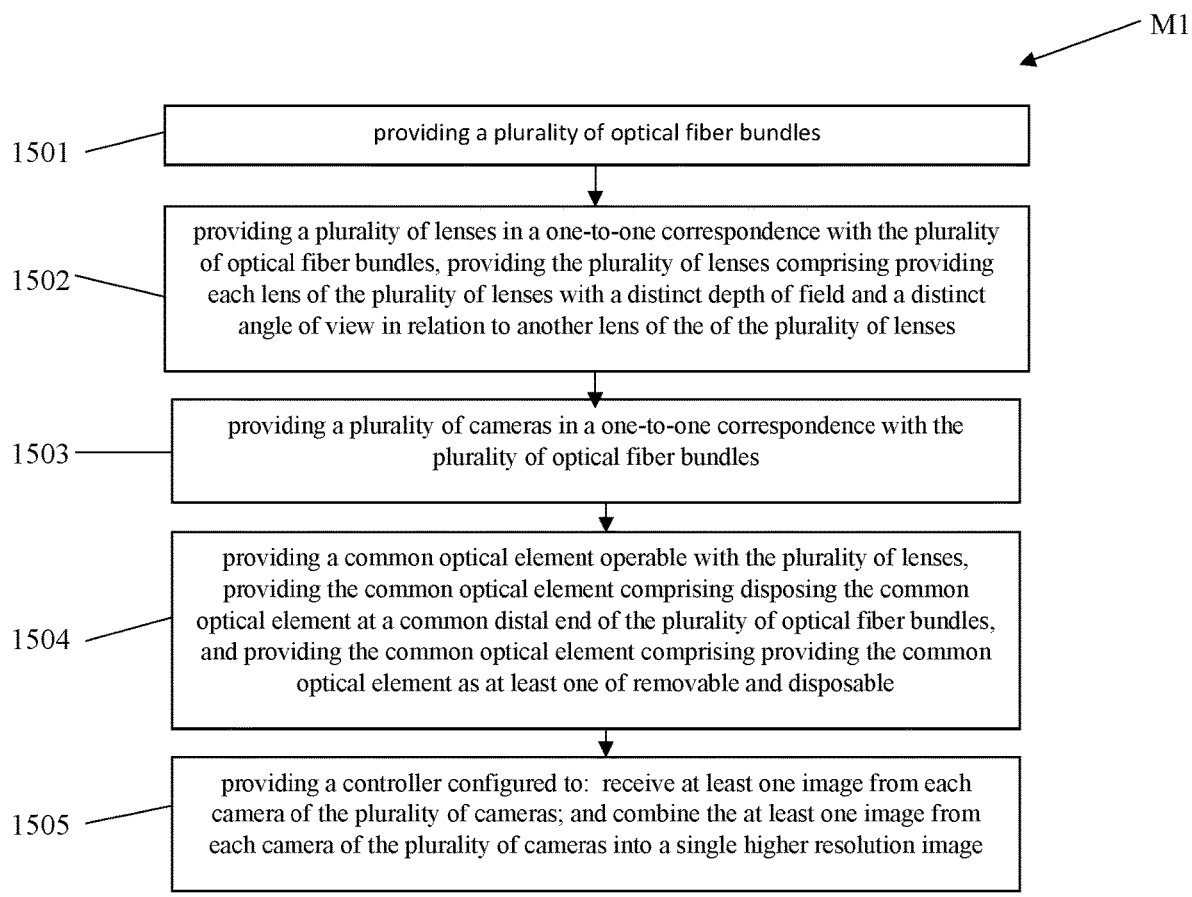
FIG. 15 is a flow diagram illustrating a method of providing an endoscope apparatus, as shown in FIG. 14, in accordance with an embodiment of the present disclosure.

Referring to FIG. 15, this flow diagram illustrates a method M1 of providing an endoscope apparatus A, as shown in FIG. 14, in accordance with an embodiment of the present disclosure. The method M1 comprises: providing a plurality of optical fiber bundles 1401, as indicated by block 1501; providing a plurality of lenses 1402 in a one-to-one correspondence with the plurality of optical fiber bundles 1401, providing the plurality of lenses 1402 comprising providing each lens 1402 of the plurality of lenses 1402 with a distinct depth of field and a distinct angle of view in relation to another lens 1402 of the plurality of lenses 1402, as indicated by block 1502; and providing a plurality of cameras 1403 in a one-to-one correspondence with the plurality of optical fiber bundles 1401, as indicated by block 1503. The method M1 further comprises providing a common optical element 1404 operable with the plurality of lenses 1402, providing the common optical element 1404 comprising disposing the common optical element 1404 at a common distal end of the plurality of optical fiber bundles 1401, and providing the common optical element 1404 comprising providing the common optical element 1404 as at least one of removable and disposable, as indicated by block 1504.

Still referring to FIG. 15, in the method M1, providing the plurality of lenses 1402, as indicated by block 1502, comprises disposing each lens in the common optical element 1404. Providing the plurality of lenses 1402, as indicated by block 1502, comprises correspondingly disposing each lens 1402 of the plurality of lenses 1402 at a distal end of each optical fiber bundle 1401 of the plurality of optical fiber bundles 1401. Providing the plurality of cameras 1403, as indicated by block 1503, comprises correspondingly disposing each camera 1403 at a proximal end of each optical fiber bundle 1401 of the plurality of optical fiber bundles 1401. Providing the plurality of optical fiber bundles 1401, as indicated by block 1501, comprises coupling, together, the plurality of optical fiber bundles 1401 at the common distal end. Providing the plurality of optical fiber bundles 1401, as indicated by block 1501, comprises providing each optical fiber bundle 1401 with a largest bending radius defining a largest bending radius of the apparatus A. Providing the plurality of optical fiber bundles 1401, as indicated by block 1501, comprises providing a first optical fiber bundle and providing a second optical fiber bundle. Providing the plurality of optical fiber bundles 1401, as indicated by block 1501, providing the plurality of lenses 1402, as indicated by block 1502, and providing the plurality of cameras 1403, as indicated by block 1503, together, providing a three-dimensional camera. Providing the plurality of optical fiber bundles 1401, as indicated by block 1501, comprises spacing-apart each optical fiber bundle distal end from another optical fiber bundle distal end and providing the plurality of lenses 1402 comprises spacing-apart each lens 1402 from another lens 1402 to provide a plurality of distinct views.

Still referring to FIG. 15, in the method M1, providing the plurality of lenses 1402, as indicated by block 1502, comprises providing each lens 1402 of the plurality of lenses 1402 with a distinct field of view in relation to another lens 1402 of the plurality of lenses 1402. The method M1 further comprises providing a controller 1405 configured to: receive at least one image from each camera 1403 of the plurality of cameras 1403; and combine the at least one image from each camera 1403 of the plurality of cameras 1403 into a single higher resolution image, as indicated by block 1505. Providing the controller 1405, as indicated by block 1505, comprises further configuring the controller 1405 to remove dead pixels from the at least one image from each camera 1403 of the plurality of cameras 1403. Providing the controller 1405, as indicated by block 1505, further comprises configuring the controller 1405 to provide a depth map by combining the at least one image from each camera 1403 of the plurality of cameras 1403. Providing the controller 1405, as indicated by block 1505, further comprises configuring the controller 1405 to provide the depth map by using light field processing. Providing the plurality of optical fiber bundles 1401, as indicated by block 1501, comprises providing each optical fiber bundle 1401 with a diameter in a range of up to approximately 2 mm. Providing the common optical element 1404, as indicated by block 1504, comprises providing a body having a proximal end and a distal end. Providing the body comprises configuring the distal end of the body to accommodate the plurality of lenses 1402. Providing the body comprises providing the proximal end of the body with a plurality of slots configured to correspondingly receive the plurality of optical fiber bundles 1401, each slot of the plurality of slots correspondingly terminating at each lens of the plurality of lenses 1402 at the distal end of the body.

Figure 16:
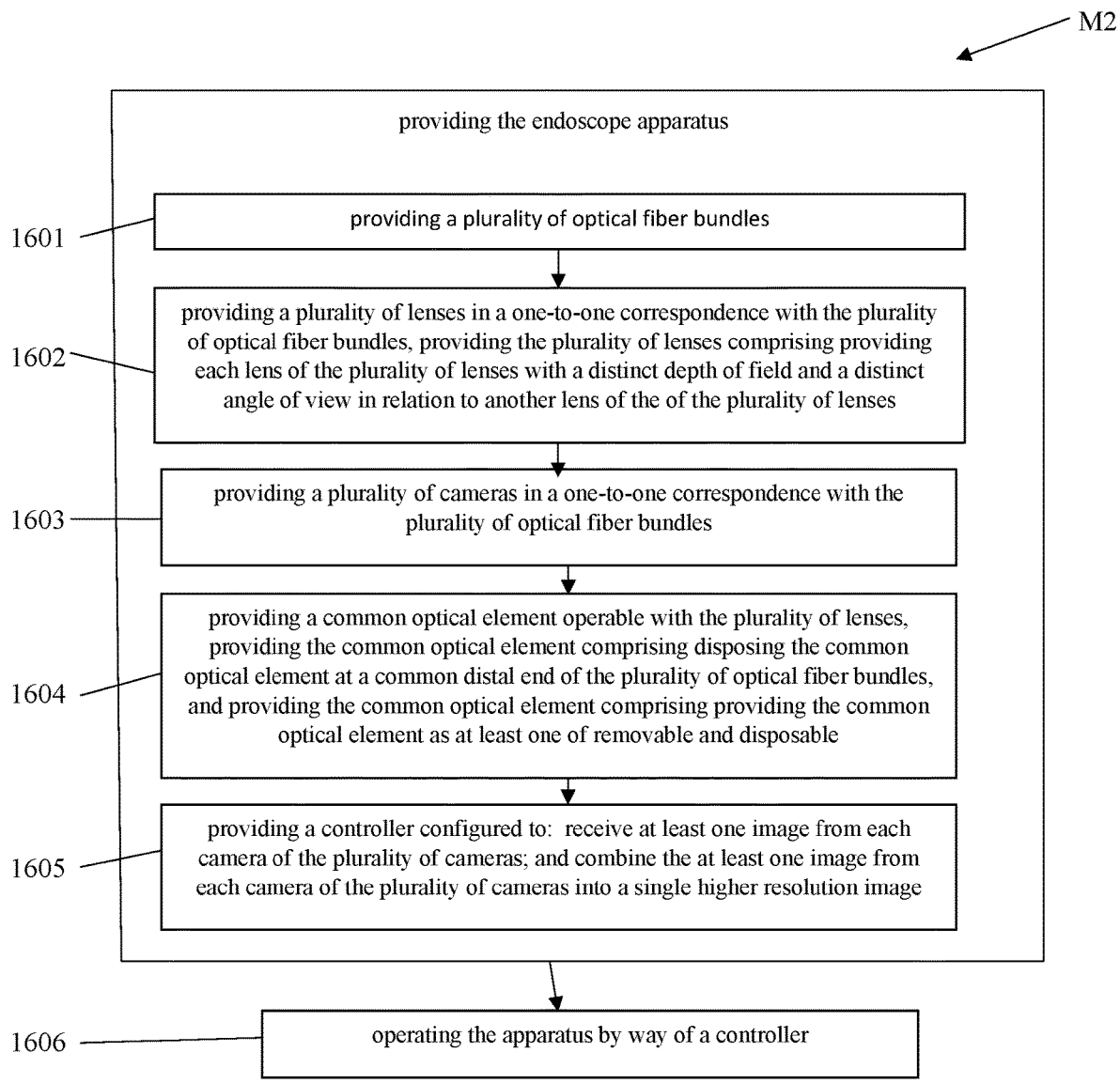
FIG. 16 is a flow diagram illustrating a method of imaging by way of an endoscope apparatus, as shown in FIG. 14, in accordance with an embodiment of the present disclosure.

Referring to FIG. 16 is a flow diagram illustrates a method M2 of imaging by way of an endoscope apparatus A, as shown in FIG. 14, in accordance with an embodiment of the present disclosure. The method M2 comprises: providing the apparatus A, as indicated by block 1600, providing the apparatus A comprising: providing a plurality of optical fiber bundles 1401, as indicated by block 1601; providing a plurality of lenses 1402 in a one-to-one correspondence with the plurality of optical fiber bundles 1401, providing the plurality of lenses 1402 comprising providing each lens 1402 of the plurality of lenses 1402 with a distinct depth of field and a distinct angle of view in relation to another lens 1402 of the plurality of lenses 1402, as indicated by block 1602; and providing a plurality of cameras 1403 in a one-to-one correspondence with the plurality of optical fiber bundles 1401, as indicated by block 1603; and operating the apparatus A by way of a controller, e.g., the controller 1405, as indicated by block 1606. The method M2 further comprises: providing a common optical element 1404 operable with the plurality of lenses 1402, providing the common optical element 1404 comprising disposing the common optical element 1404 at a common distal end of the plurality of optical fiber bundles 1401, and providing the common optical element 1404 comprising providing the common optical element 1404 as at least one of removable and disposable, as indicated by block 1604; and providing a controller configured to: receive at least one image from each camera 1403 of the plurality of cameras 1403; and combine the at least one image from each camera 1403 of the plurality of cameras 1403 into a single higher resolution image, as indicated by block 1605.

Hence, provided herein is a flexible endoscope that comprises of multiple optical fiber bundles which can each have about 18 kilopixels resolution, each coupled to a multi-lens array at a distal end and multiple cameras at a proximal end. Each lens on the array can convey a separate image to the distal end of each optical fiber bundle and cameras coupled to the proximal end of the optical fiber bundles acquire separate pixelated images. These lower resolution images, acquired by each of the cameras, can be merged and/or combined, and reconstructed using principles of light field imaging and processing, to produce a super-resolution image. This can allow for much higher resolution imaging than conventional endoscopes, which can allow for better diagnosis and treatment.

Furthermore, using light field processing of the separate images from the cameras, a depth-map of objects imaged by the lenses can be reconstructed, which can allow structures with differing depth to be more easily detected and/or seen. By taking advantage of the underlying optics of the method, omni-focusing (having all object in the scene in-focus), selective post-acquisition focusing, and depth of field control is possible post-acquisition and real-time. This post-processing can allow for removal of "dead" pixels which can be caused by broken fibers within fiber bundles without significant loss of detail. Using separate fiber bundles can also resolve flexibility issues associated with having one large fiber bundle since each smaller fiber bundle can move independently from one another and not seize when bent.

While devices and methods described herein have been described with respect to surgical and/or medical applications, devices and methods described herein can be used in other fields, such as in engineering and defense, particularly in scenarios where high-resolution three-dimensional imaging of a space and/or objects occurs through a small, (and even convoluted) access port. The specific embodiments described above have been shown by way of example, and it should be understood that these embodiments may be susceptible to various modifications and alternative forms. The claims are not intended to be limited to the particular forms disclosed, but, rather, to cover all modifications, equivalents, and alternatives falling within the spirit and scope of the present disclosure.

What is claimed:

1. An endoscope apparatus, the apparatus comprising:
a plurality of optical fiber bundles;
a plurality of lenses in a one-to-one correspondence with the plurality of optical fiber bundles, each lens of the plurality of lenses comprising a distinct depth of field and a distinct angle of view in relation to another lens of the plurality of lenses;
a plurality of cameras in a one-to-one correspondence with the plurality of optical fiber bundles; and
a common optical element operable with the plurality of lenses, the common optical element disposed at a common distal end of the plurality of optical fiber bundles, and the common optical element being at least one of removable and disposable.

2. The apparatus of claim 1, wherein:
each lens of the plurality of lenses is disposed in the common optical element,
each lens of the plurality of lenses is correspondingly disposed at a distal end of each optical fiber bundle of the plurality of optical fiber bundles,
each camera of the plurality of cameras is correspondingly disposed at a proximal end of each optical fiber bundle of the plurality of optical fiber bundles,
the plurality of optical fiber bundles is coupled, together, with at the common distal end,
each optical fiber bundle of the plurality of optical fiber bundles comprises a largest bending radius defining a largest bending radius of the apparatus,
the plurality of optical fiber bundles comprises a first optical fiber bundle and a second optical fiber bundle,
the plurality of optical fiber bundles, the plurality of lenses, and the plurality of cameras, together, forming a three-dimensional camera, and
each optical fiber bundle distal end is spaced apart from another optical fiber bundle distal end and each lens is spaced apart from another lens to provide a plurality of distinct views.

3. The apparatus of claim 1, wherein each lens of the plurality of lenses further comprises a distinct field of view in relation to another lens of the plurality of lenses.

4. The apparatus of claim 1, further comprising a controller configured to: receive at least one image from each camera of the plurality of cameras; and combine the at least one image from each camera of the plurality of cameras into a single higher resolution image.

5. The apparatus of claim 4, wherein the controller is further configured to remove dead pixels from the at least one image from each camera of the plurality of cameras.

6. The apparatus of claim 4, wherein the controller is further configured to provide a depth map by combining the at least one image from each camera of the plurality of cameras.

7. The apparatus of claim 6, wherein the controller is further configured to provide the depth map by using light field processing.

8. The apparatus of claim 1, wherein each optical fiber bundle of the plurality of optical fiber bundles comprises a diameter in a range of up to approximately 2 mm.

9. The apparatus of claim 1, wherein the common optical element comprises a body having a proximal end and a distal end, the distal end of the body configured to accommodate the plurality of lenses, and the proximal end of the body comprising a plurality of slots configured to correspondingly receive the plurality of optical fiber bundles, each slot of the plurality of slots correspondingly terminating at each lens of the plurality of lenses at the distal end of the body.

10. A method of providing an endoscope apparatus, the method comprising:
providing a plurality of optical fiber bundles;
providing a plurality of lenses in a one-to-one correspondence with the plurality of optical fiber bundles, providing the plurality of lenses comprising providing each lens of the plurality of lenses with a distinct depth of field and a distinct angle of view in relation to another lens of the plurality of lenses;

providing a plurality of cameras in a one-to-one correspondence with the plurality of optical fiber bundles;

providing a common optical element operable with the plurality of lenses, providing the common optical element comprising disposing the common optical element at a common distal end of the plurality of optical fiber bundles, and providing the common optical element comprising providing the common optical element as at least one of removable and disposable.

11. The method of claim 10, wherein:

providing the plurality of lenses comprises disposing each lens in the common optical element, providing the plurality of lenses comprises correspondingly disposing each lens of the plurality of lenses at a distal end of each optical fiber bundle of the plurality of optical fiber bundles, providing the plurality of cameras comprises correspondingly disposing each camera at a proximal end of each optical fiber bundle of the plurality of optical fiber bundles, providing the plurality of optical fiber bundles comprises coupling, together, the plurality of optical fiber bundles at the common distal end, providing the plurality of optical fiber bundles comprises providing each optical fiber bundle with a largest bending radius defining a largest bending radius of the apparatus, providing the plurality of optical fiber bundles comprises providing a first optical fiber bundle and providing a second optical fiber bundle, providing the plurality of optical fiber bundles, providing the plurality of lenses, and providing the plurality of cameras, together, providing a three-dimensional camera, and providing the plurality of optical fiber bundles comprises spacing-apart each optical fiber bundle distal end from another optical fiber bundle distal end and providing the plurality of lenses comprises spacing-apart each lens from another lens to provide a plurality of distinct views.

12. The method of claim 10, wherein providing the plurality of lenses comprises providing each lens of the plurality of lenses with a distinct field of view in relation to another lens of the plurality of lenses.

13. The method of claim 10, further comprising providing a controller configured to: receive at least one image from each camera of the plurality of cameras; and combine the at least one image from each camera of the plurality of cameras into a single higher resolution image.

14. The method of claim 10, wherein providing the controller is further configuring the controller to remove dead pixels from the at least one image from each camera of the plurality of cameras.

15. The method of claim 13, wherein providing the controller is further configuring the controller to provide a depth map by combining the at least one image from each camera of the plurality of cameras.

16. The method of claim 15, wherein providing the controller is further configuring the controller to provide the depth map by using light field processing.

17. The method of claim 10, wherein providing the plurality of optical fiber bundles comprises providing each optical fiber bundle with a diameter in a range of up to approximately 2 mm, and wherein providing the common optical element comprises providing a body having a proximal end and a distal end, providing the body comprising configuring the distal end of the body to accommodate the plurality of lenses, and providing the body comprising providing the proximal end of the body with a plurality of slots configured to correspondingly receive the plurality of optical fiber bundles, each slot of the plurality of slots correspondingly terminating at each lens of the plurality of lenses at the distal end of the body.

18. A method of imaging by way of an endoscope apparatus, the method comprising:

providing the apparatus, providing the apparatus comprising:

providing a plurality of optical fiber bundles;

providing a plurality of lenses in a one-to-one correspondence with the plurality of optical fiber bundles, providing the plurality of lenses comprising providing each lens of the plurality of lenses with a distinct depth of field and a distinct angle of view in relation to another lens of the plurality of lenses; and providing a plurality of cameras in a one-to-one correspondence with the plurality of optical fiber bundles;

operating the apparatus by way of a controller;

providing a common optical element operable with the plurality of lenses, providing the common optical element comprising disposing the common optical element at a common distal end of the plurality of optical fiber bundles, and providing the common optical element comprising providing the common optical element as at least one of removable and disposable.

* * * * *